US 6,587,724 B2

(12) United States Patent
Mann

(10) Patent No.: US 6,587,724 B2
(45) Date of Patent: Jul. 1, 2003

(54) MAGNITUDE PROGRAMMING FOR IMPLANTABLE ELECTRICAL STIMULATOR

(75) Inventor: Carla M. Mann, Los Angeles, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 288 days.

(21) Appl. No.: 09/740,339

(22) Filed: Dec. 18, 2000

(65) Prior Publication Data

US 2001/0034542 A1 Oct. 25, 2001

Related U.S. Application Data

(60) Provisional application No. 60/172,167, filed on Dec. 17, 1999.

(51) Int. Cl.$^7$ ................................................. A61N 1/36
(52) U.S. Cl. ............................................ 607/30; 607/59
(58) Field of Search ......................... 607/2, 45, 46, 607/56, 116, 137, 30, 9, 57, 62, 59, 99, 29; 600/378, 544

(56) References Cited

U.S. PATENT DOCUMENTS

| 4,279,258 A | * | 7/1981 | John ........................... 600/544 |
| 5,603,726 A | | 2/1997 | Schulman et al. ............. 607/57 |
| 5,626,629 A | | 5/1997 | Faltys et al. .................. 607/57 |
| 5,797,970 A | | 8/1998 | Pouvreau ...................... 607/9 |
| 5,895,416 A | | 4/1999 | Barreras, Sr. et al. ........ 607/62 |
| 5,913,882 A | | 6/1999 | King ............................ 607/62 |
| 5,957,958 A | * | 9/1999 | Schulman et al. ............. 607/56 |
| 6,052,624 A | | 4/2000 | Mann ........................... 607/46 |
| 6,181,969 B1 | | 1/2001 | Gord ............................ 607/59 |
| 6,253,109 B1 | * | 6/2001 | Gielen .......................... 607/45 |
| 6,393,325 B1 | * | 5/2002 | Mann et al. .................. 607/46 |

FOREIGN PATENT DOCUMENTS

WO    9709863    3/1997

\* cited by examiner

*Primary Examiner*—Tu Ba Hoang
(74) *Attorney, Agent, or Firm*—Bryant R. Gold

(57) ABSTRACT

A neural stimulation system allows the magnitude of electrical stimuli generated by the system to be programmed to a desired level greater than or equal to a minimum perceived threshold and less than or equal to a maximum tolerable perceived threshold. The electrical stimuli are applied through selected groupings of individual electrode contacts of a multi-electrode-contact electrode array attached to pulse generation circuitry as either cathodes or anodes. The electrode array is implanted so that the individual electrode contacts are in contact with the body tissue to be stimulated. Stimulating electrical current pulses, defined by a prescribed set of stimulus parameters are generated and applied to the selected electrode contacts so as to flow from the anode electrodes to the cathode electrodes. The perceived magnitude of the applied stimuli is equalized in order to enable quick, automated, and/or interactive programming of the values of the stimulation parameters.

23 Claims, 7 Drawing Sheets

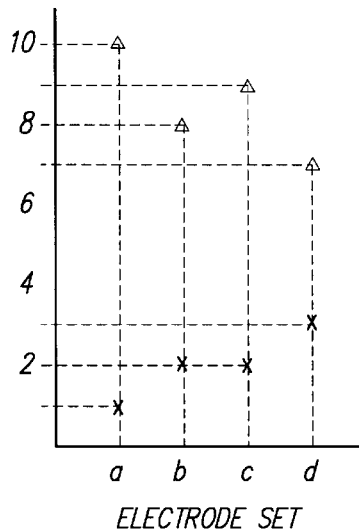
FIG. 3A
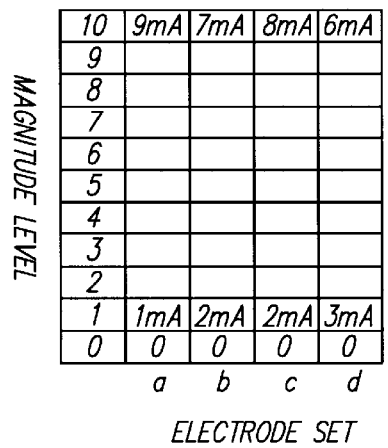
FIG. 3B
```
       E=1
E1 OR E2   P   M   X=1   X=2   X=3   X=4   X=5   X=6   X=7   X=8   X=9   X=10
       E1  2   8    2   2.67  3.33    4   4.67  5.33    6   6.67  7.33    8
       E2  3   7    3   3.44  3.89  4.33  4.78  5.22  5.67  6.11  6.56    7
       E=2
E1 & E2    P   M   X=1   X=2   X=3   X=4   X=5   X=6   X=7   X=8   X=9   X=10
       E1  2   8    1   1.33  1.67    2   2.33  2.67    3   3.33  3.67    4
       E2  3   7   1.5  1.72  1.94  2.17  2.39  2.61  2.83  3.06  3.28   3.5
       SUM          2.5  3.06  3.61  4.17  4.72  5.28  5.83  6.39  6.95   7.5
```
FIG. 6

MAGNITUDE PROGRAMMING FOR IMPLANTABLE ELECTRICAL STIMULATOR

This application claims the benefit of U.S. Provisional Application Ser. No. 60/172,167, filed Dec. 17, 1999, which application is incorporated herein by reference.

BACKGROUND OF THE INVENTION

The present invention relates to implantable stimulators, e.g., an implantable neural stimulator, and more particularly to a system and method for programming the magnitude (e.g., amplitude) of the stimulation pulses that are generated by such neural stimulator. The invention may be used with a wide variety of neural stimulators, e.g., spinal cord stimulators, brain stimulators, urinary incontinence stimulators, cochlear stimulators, and the like.

Neural stimulation systems of the type with which the present invention may be used are described in the art, e.g., in U.S. Pat. No. 5,603,726. Such stimulator systems typically include: (1) an implantable pulse generator; (2) an electrode array connected to the implantable pulse generator; and (3) some means, e.g., an external programmer, for controlling or programming the implantable pulse generator. In operation, the implantable pulse generator generates an electrical stimulation pulse, or pulse sequence, in accordance with a prescribed pattern or stimulation strategy. Each pulse may be programmed or set to a desired magnitude (amplitude and/or pulse width), and applied at a set or programmed rate (or frequency) to surrounding body tissue through a selected pair or grouping of electrode contacts of a multiple electrode array.

U.S. Pat. No. 5,895,416 teaches one type of method and apparatus for controlling and steering an electric field. The '416 patent steers the size and location of the electric field in order to recruit only target nerve tissue and exclude unwanted nerve tissue. Such steering is done by changing the voltage amplitude at each anode in response to changes in electrode impedance of an electrode array in order to maintain a constant anodic current.

Unfortunately, programming implantable stimulators that have multi-electrode contacts can be a very time consuming task. This is particularly true for a spinal cord stimulation system, or similar system, where there are typically 8 to 16 electrode contacts on the electrode array through which the stimulation pulses are applied to the spinal nerves. With 8 to 16 electrode contacts there are thousands and thousands of possible electrode combinations. The goal of programming a spinal cord stimulator, or similar neural stimulator, is to figure out which electrode combinations of the thousands that are possible should be used to apply electrical stimulus pulses (each of which can theoretically be programmed to have a wide range of amplitudes, pulse widths, and repetition rates) so as to best serve the patient's needs. More particularly, the goal of programming a spinal cord stimulator, or other neural stimulator, is to optimize the electrode combination of anodes and cathodes, as well as the amplitude, pulse width and rate of the applied stimulation pulses, so as to allow the stimulator to best perform its intended function, e.g., in the case of a spinal cord stimulator, to relieve pain felt by the patient. The manual selection of each electrode combination and the stimulus parameters that are used with such electrode combination (where the "stimulus parameters" include amplitude, pulse width, and repetition rate or frequency) is an unmanageable task. What is needed is a system and method for programming a neural stimulator, such as a spinal cord stimulator, that automates much of the programming process using interactive programs, and in particular wherein the amplitude of the applied stimulus may be programmed in a way that facilitates the use of automated and interactive programs safely and effectively.

A disadvantage associated with many existing neural stimulators is that such systems cannot independently control the amplitude for every electrode in a stimulating group of electrodes, or "channel". Thus, stimulation fields cannot be highly controlled with multiple stimulating electrodes. Instead, a constant voltage is applied to all electrodes assigned to stimulate a target site at any given time (wherein the electrodes thus assigned are referred to as a "channel"). While such approach may make programming such stimulator a much more manageable task (because the number of possible electrodes and parameter choices are severely limited), such limitations may prevent the stimulator from providing the patient with an optimal stimulation regimen. What is needed, therefore, is a neural stimulator wherein all of the possible electrode combinations and parameter settings can be used, and wherein a programming technique exists for use with such neural stimulator whereby an optimum selection of electrode combinations and parameters settings may be quickly and safely identified and used.

To illustrate the problem that a clinician or other medical personnel faces when programming a typical neural stimulator wherein each electrode on an electrode array may be tested, consider the following example. The clinician typically performs an electrode test in terms of the patient's response, e.g., by selecting a set of electrodes (assigning anodes and cathodes), setting a pulse width and rate, and by then increasing the amplitude until the patient begins to feel stimulation. The clinician continues to increase the stimulation amplitude until the stimulation is strongly felt, and then the patient is asked the location where the stimulation is felt. The stimulation is then turned off and the steps are repeated for the next electrode set, until the clinician has a good map of the stimulation coverage by an electrode array. Disadvantageously, however, the clinician cannot simply jump from one set of electrodes within the array to a next set of electrodes within the array and back again while the stimulation is turned on because the perception thresholds vary. What is needed is a system or apparatus that does not require that the clinician turn off the stimulation and start over, increasing the amplitude for each electrode set, but rather allows the clinician to compare back and forth between electrode sets while continuously obtaining patient feedback. What is further needed is a system or apparatus wherein the clinician does not have to start over every time he or she repeats a formerly-tested electrode set. Unfortunately, with current programming approaches, because there is no means to automatically adjust the magnitude of stimulation, the clinician must start over every time another electrode set is selected.

The threshold ranges derived from such clinician tests usually vary from one electrode to the next. That is, at a given pulse width the perception threshold at a first electrode may be 2 milliamps (mA), (or 2 volts (V) at 1000 ohms), with a maximum tolerable threshold of 7 mA (or 7 V at 1000 ohms). At that same pulse width, the perception threshold at a second electrode may be 3 mA (or 3 V at 1000 ohms), with a maximum tolerable threshold of 6 mA (or 6 V at 1000 ohms). Thus, switching from one electrode to the next at a constant current or voltage level may not be done without the patient feeling perceptual intensity differences. Moreover, automatically switching between electrodes at constant parameter outputs could result in unintentionally exceeding the maximum tolerable threshold associated with a particular electrode where the maximum tolerable threshold of the electrode is less than the maximum tolerable threshold of another electrode. As a result, the typical method for testing electrode combinations, as described above, is to start with the output at zero for every combination of electrodes (including combinations which result in too many combinations to test), and gradually increase the amplitude to a comfortable level, and then have the patient respond to paresthesia or other coverage. No quick or rapid electrode switching can be done. It is thus evident that what is needed is a system and method of equalizing the perceived amplitude, and to thereby enable quick, automated, and/or interactive (i.e., directional programming) methods.

SUMMARY OF THE INVENTION

The present invention addresses the above and other needs by providing a system and method for programming the magnitude of electrical stimuli generated and applied by a neural stimulator. e.g., a spinal cord stimulator. The electrical stimuli are applied through selected groupings of individual electrode contacts of a multi-electrode-contact electrode array attached to pulse generation circuitry as either cathodes or anodes. The electrode array is implanted so that the individual electrode contacts are in contact with the body tissue to be stimulated. Stimulating electrical current pulses, defined by a prescribed set of stimulus parameters, e.g., pulse amplitude, pulse width and pulse repetition rate, are generated and applied to the selected electrode contacts so as to flow from the anode electrodes to the cathode electrodes. As the current pulses flow through the body tissue, the electrical current causes the neural stimulator to carry out its intended function, e.g, triggering a desired neural response or blocking an undesired neural activity. The present invention advantageously provides a programming system or method whereby the perceived magnitude of the applied stimuli is equalized in order to enable quick, automated, and/or interactive selection of the stimulation parameter values that are used by the stimulator.

In accordance with one aspect of the invention, the invention may thus be characterized as a method of operating an implantable neural stimulator. The implantable neural stimulator with which such method is used typically includes a programmable pulse generator circuit that is housed within a sealed case. An electrode array is connected to the neural stimulator. The sealed case may function as a reference electrode for some electrode configurations. The electrode array has a plurality of electrode contacts, identified as electrodes 0, 1, . . . n, where n is an integer of at least one (so that electrodes 0 and 1 comprise the at least two electrodes). In one embodiment, for example, n may be an integer of, e.g., three (so that there are four electrodes, electrodes 0, 1, 2 and 3). In another embodiment, n may be an integer of, e.g., 15 (so that there are sixteen electrodes, electrodes 0, 1, 2, . . . 15). The invention may be used with any number n of electrodes.

The method of operating the neural stimulator, broadly stated, comprises: (a) measuring and recording at least one perception point, e.g., a minimum perception threshold level or a comfortable threshold level, for all of the electrode contacts and combinations thereof, or (where the number of electrode contacts and combinations thereof is too large to measure) measuring at least one perception point for a selected subset of the electrode contacts and combinations; (b) estimating and recording perception points for unmeasured electrode contacts or sets of electrode contacts; and (c) mapping the recorded measured and/or estimated values to magnitude levels for use with other designated stimulation parameters.

In accordance with another aspect of the invention, the invention may be characterized as a neural stimulation system wherein an optimal set of stimulus parameters may be determined and programmed into the system. Such system includes: (a) an implantable neural stimulator comprising a sealed case, and having pulse generation circuitry contained inside of the case that is adapted to generate a stimulus pulse in accordance with programmed stimulus parameters; (b) an electrode array having a multiplicity of electrode contacts, wherein each of the multiplicity of electrode contacts may be selectively connected to the pulse generation circuitry within the implantable neural stimulator; (c) a known threshold level, e.g., a known perception threshold level, a known comfortable threshold level, and/or a known maximum tolerable threshold level, for at least a plurality of the multiplicity of electrode contacts, where such known threshold levels are typically expressed in units of current or voltage; and (d) an equalizer circuit or system or technique (hereafter referred to simply as an "equalizer") that equalizes the threshold level(s) to unit-less magnitude levels. In a preferred embodiment, the equalizer further estimates corresponding unit-less magnitude levels for any electrode contacts, or combination of electrode contacts, for threshold levels not initially known or measured. Once the unit-less magnitude levels are known or estimated for each electrode within a given electrode set, the neural stimulation system may thereafter automatically set or adjust the magnitude of the stimulus applied through the given electrode set when such given electrode set is selected as the electrode set through which stimulation is to be applied. Advantageously, such neural stimulation system allows stimulation to be applied through different electrode sets without having to ramp the amplitude up from a zero value for each electrode set selected. Hence, a clinician using such neural stimulation system may immediately jump between two or more electrode sets, each of which has the stimulation magnitude levels automatically adjusted to, e.g., a minimum perception threshold level, a maximum tolerable threshold level, or a selected value between the minimum perception and maximum tolerable threshold levels, as different stimulus parameters are tested.

Any of numerous techniques and approaches known in the art may be used to measure perception threshold and maximum tolerable thresholds. Similarly, any one of numerous stimuli-application circuits and testing techniques known and practiced in the art may be used for applying a stimulus of a prescribed magnitude to one or more electrodes and testing whether such application produces a desired result. For an SCS system, the desired result will typically involve determining, e.g., whether the resulting paresthesia sensed by the patient sufficiently blocks pain felt by the patient.

The "equalizer" referenced in the system described above is at the heart of the present invention. Such equalizer advantageously equalizes the perception threshold measurement and the maximum tolerable threshold measurement to unit-less magnitude levels for all of the electrode contacts such that level x of one electrode configuration has an equal intensity perception as another electrode configuration set at level x. Once such equalization has been performed, the magnitude levels may thereafter be used to set the magnitude of the stimulation levels without the need to manually ramp up or ramp down the stimulus magnitude at each electrode contact, as is required in the prior art.

The equalizer may be realized in software, firmware, or hardware. Typically, equalization is performed by (i) storing the perception threshold measurement and the maximum tolerable threshold measurement for each electrode contact; (ii) mapping the perception threshold measurement of each electrode contact to a first number magnitude level; and (iii) mapping the maximum tolerable threshold measurement to a second number magnitude level. A stimulus having the first number magnitude level causes an electrode contact receiving that stimulus to receive a stimulus having a magnitude equal to the perception threshold measurement for that electrode contact. Similarly, a stimulus having the second number magnitude level causes an electrode contact receiving that stimulus to receive a stimulus having a magnitude equal to the maximum tolerable threshold measurement for that electrode contact. In a preferred implementation, the first number magnitude level is assigned to be a low value, e.g., "1", and the second number magnitude level is assigned to be a higher value, e.g., "10". A stimulus having a magnitude level greater than "1" and less than "10" causes a stimulus to be applied that is somewhere between the perception threshold and maximum tolerable threshold. Typically, the stimulus magnitude increases as the magnitude level number (which is a unit-less number) increases. That is, a magnitude level "m" causes a stimulus to be generated that has a magnitude greater than a stimulus having a magnitude level "m−1", where m is an integer of from 1 to 10, and where a magnitude level "0" stimulus comprises a stimulus having zero magnitude.

Where there are a large number of electrode contacts, making it impractical to measure threshold levels for all possible combinations of the electrode contacts, only a subset of the possible electrode contacts need to be measured, and thereafter the unit-less magnitude levels for the non-measured electrode contacts may be estimated. For example, it there are sixteen electrode contacts arranged in line within a linear array, it would typically only be necessary to measure threshold levels, and assign corresponding unit-less magnitude levels, for the two electrode contacts at the edges of the array. Unit-less magnitude levels may then be estimated for the electrode contacts that reside between the outer two electrode contacts using an appropriate estimation algorithm, such as a linear extrapolation.

Further, it is not always necessary to measure, for a given electrode configuration for which a measurement is being made, both the minimum perception threshold level and the maximum tolerable threshold level. Rather, in many instances, all that is required is to measure a single threshold level, e.g., a comfortable threshold level, from which single threshold measurement a corresponding unit-less magnitude threshold level may be assigned, and from which other unit-less magnitude levels may be estimated for electrode contacts similarly configured. For example, where the unit-less magnitude levels range from "1" (corresponding to the minimum perception threshold level) to "10" (corresponding to a unit-less magnitude level "10"), a comfortable unit-less magnitude level "5" could be equalized with a proportionate range approximated around the level "5" to give a reasonable operating range. This advantageously reduces the number of measured points required, but disadvantageously is less accurate.

A principle advantage offered by the invention is the ability to dynamically switch between electrode sets while the stimulation is continuously applied. Such advantage allows immediate comparisons of stimulation to be made without having to reset the stimulation magnitude, and while maintaining a relatively constant perception of intensity or magnitude of stimulation, thereby avoiding over or under stimulation.

Further, the invention does not require that threshold measurements be taken for all possible electrode configurations. Rather, a subset of the possible electrode configurations may be measured, and from such measurements estimates may be made of the unmeasured thresholds with relative accuracy. For example, unit-less threshold levels for bipolar, monopolar, tripolar, and multipolar combinations may be readily estimated from actual threshold measurements taken from a subset of tested electrodes.

A feature of the invention is the ability to store adjustments made to stimulation levels for estimated electrode thresholds so that the system learns corrections to the estimated equalized levels.

Another feature of the invention is the ability of the system to adjust and compensate the perception stimulus when the pulse width is changed.

BRIEF DESCRIPTION OF THE DRAWINGS

The above and other aspects, features and advantages of the present invention will be more apparent from the following more particular description thereof, presented in conjunction with the following drawings wherein:

FIG. 3A illustrates perception threshold data and maximum tolerable threshold data obtained from four different electrodes;

FIG. 3B conceptually depicts the manner in which the perception and maximum tolerable threshold data gathered in FIG. 3A may be mapped into unit-less magnitude "level" settings as part of a magnitude equalizing function performed in accordance with the invention;

FIG. 6 is a table the quantitatively depicts the data represented in the FIG. 5 in tabular form;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention may be used with many different types of neural stimulators. By way of illustration, the invention will be described in terms of a spinal cord stimulator system (SCS). However, it is to be understood that the invention is not limited to use only with a SCS, but may also be used with other types of multi-electrode neural stimulators, e.g., a deep brain stimulator, a functional electrical stimulator (FES), a cochlear stimulator, or the like.

It is also to be noted that the preferred manner of adjusting the magnitude of the stimulus applied by the neural stimulator is through adjustment of the stimulus amplitude. However, as is known to those of skill in the art, amplitude is only one measure of magnitude. The magnitude of a stimulus may also be adjusted, e.g., by adjusting the width or duration of the stimulus pulse, by adjusting the duty cycle associated with a burst of pulses, by adjusting the repetition rate of the applied stimulus (if a single stimulus is applied) or the repetition rate of the applied burst (if a group of stimulus pulses is applied), and/or by adjusting the width, duty cycle or rate in combination with adjustments of the amplitude in various combinations. Thus, although the preferred implementation described herein for adjusting the magnitude of the applied stimulus is through adjustment of the amplitude and pulse width of the stimulus current, such is only exemplary. Any type of adjustment of the applied stimulus parameters that alters the amount of energy delivered to the tissue to be stimulated may be used to practice the invention, including, e.g., current amplitude adjustment, pulse width adjustment, duty cycle adjustment, stimulus frequency adjustment, or combinations thereof.

Figure 1:
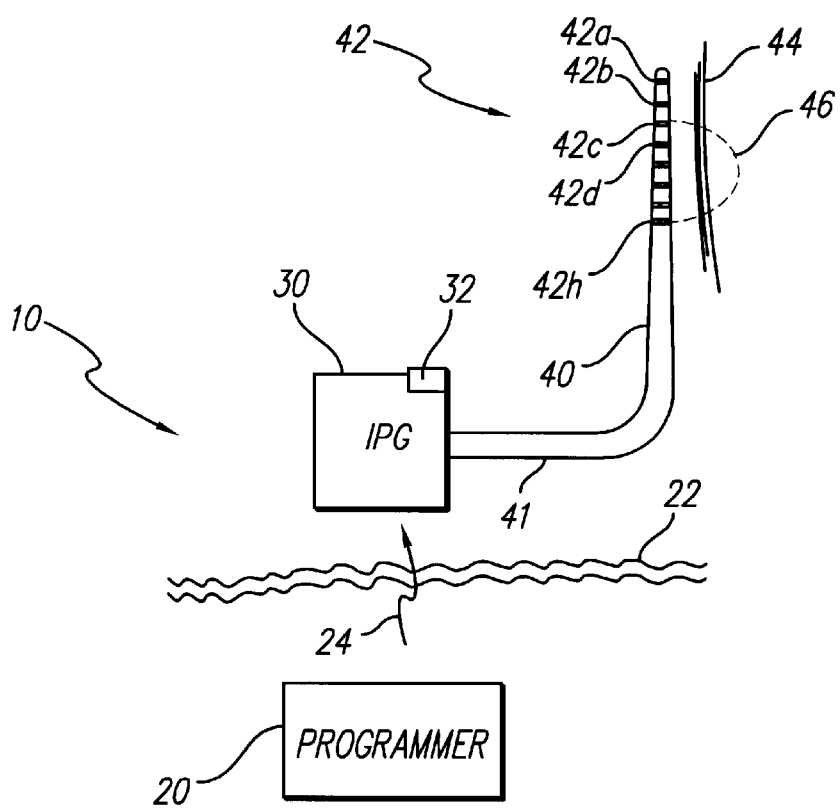
FIG. 1 shows a simplified block diagram of a neural stimulation system.

Turning first to FIG. 1, there is shown a simplified block diagram of a neural stimulation system 10. The stimulation system 10 includes an implantable pulse generator (IPG) 30 connected to an electrode array 40. The electrode array 40 comprises a flexible carrier lead body 41, typically made from silicone rubber, or some other form of Silastic® material, on which individual spaced-apart electrode contacts 42a, 42b, 42c, . . . are located near a distal end. There are eight electrode contacts illustrated in FIG. 1, contacts 42a, 42b, 42c, . . . 42h. However, this is only exemplary. Any number of electrode contacts may be used. Typically, for a spinal cord stimulator, from four to sixteen electrode contacts are used. Any number of electrode contacts 42 may be used depending upon the application. At least two electrode contacts, one of which may be included on the case of the IPG 30, must be used to produce a stimulation.

The array 40 which is shown in FIG. 1 is referred to as an "in-line" electrode array because all of the electrode contacts 42 are spaced-apart and are in line with each other along the body of the lead carrier body 41. Different types of electrode arrays may be used, e.g., various forms of paddle arrays, or combinations of in-line arrays.

Each electrode contact 42a, 42b, 42c, . . . 42h of the electrode array 40 is connected by way of a wire (not shown in FIG. 1), or other electrical conductor, embedded within the lead body to electronic pulse generation circuitry housed within the IPG 30. It is through these wires or conductors that an electrical stimulation pulse is delivered to the electrode contacts 42.

It is the purpose of the electrode array 40 to place the multiplicity of electrode contacts 42 near the body tissue that is to be stimulated. For example, in FIG. 1, a nerve fiber 44, or other similar tissue (e.g., muscle tissue), is shown as being positioned alongside the electrode array contacts 42. When one of the electrode contacts, e.g., contact 42c, is selected as an anode, and another of the electrode contacts, e.g., contact 42h, is selected as a cathode, then a stimulation current pulse, generated by the IPG 30, may flow along a current path, represented by the dotted line 46, that flows through the body tissue and the nerve fiber 44, thereby stimulating the nerves or other body tissue that come in contact with the current path. More than one electrode contact may be selected as the anode, and/or as the cathode, in such stimulation. Additionally, the IPG 30 may have a reference electrode 32 located on its case so that a stimulation current path may be set up between one or more of the electrodes 42 included within the electrode array 40 and the reference electrode 32. Such electrode configuration, wherein one of the electrode contacts is the reference electrode 32, and one of the electrodes 42 of the electrode array 40 is used as the other electrode, is referred to as monopolar stimulation. An electrode configuration where two of the electrodes 42 are used as the electrodes, one as the anode and one as the cathode, is referred to as bipolar stimulation. An electrode configuration where three of the electrodes 42 are used as the electrodes, one or two as the anode, and one or two as the cathode, is referred to as tripolar stimulation. Similarly, an electrode configuration where four or more of the electrodes 42 are used as the electrodes, at least one as the anode and at least one as the cathode, is referred to as multipolar stimulation.

Thus, it is seen that the multiplicity of electrode contacts 42 located on the electrode array 40, with or without the reference electrode 32 located on the case of the IPG 30, provide a large number of possible electrode combinations that could be used when applying stimulation pulses to the body tissue. When all of these possible electrode combinations are further combined with all of the possible parameter changes that could be made to the applied stimulus pulse(s), it is evident that the number of combinations that need to be tested in order to determine an optimum safe and efficacious combination for use by the patient is almost unmanageable. One purpose of the present invention to provide a way to quickly and safely identify which electrode combination, and which stimulus parameters, are most efficacious for a given patient.

The IPG 30 is controlled by, e.g., programmed by, an external programmer 20. The programmer 20, or a component of the programmer 20 (e.g., a programming head) is typically placed near the skin 22 of the patient in an area close to the location where the IPG 30 is implanted. Then, a suitable transcutaneous communications link, represented in FIG. 1 by the wavy arrow 24, is established between the programmer 20 and the IPG 30. Such link 24 may take many forms, any of which is suitable for purposes of the present invention. Exemplary transcutaneous links 24 may be realized, e.g., through inductive coupling, RF transmission, magnetic coupling, optical coupling, and the like.

Once the transcutaneous link 24 has been established, the programmer 20 downloads whatever programming data the IPG 30 needs in order to perform its function of generating stimulation pulses. Such data typically includes the stimulus parameters, e.g., pulse width, pulse amplitude, and pulse rate (defined below in connection with FIG. 2), and the individual electrode contacts 42 through which the electrical stimulus is to be applied to the body tissue. Such data may also include new or updated operating programs to be used by the IPG as it carries out its function of generating stimulus pulses. In many embodiments of the invention, the IPG 30 may also send status and/or other data back to the programmer 20 through a back telemetry link. When used, the back telemetry link may be the same as, or different from, the forward transcutaneous link 24.

Figure 2:
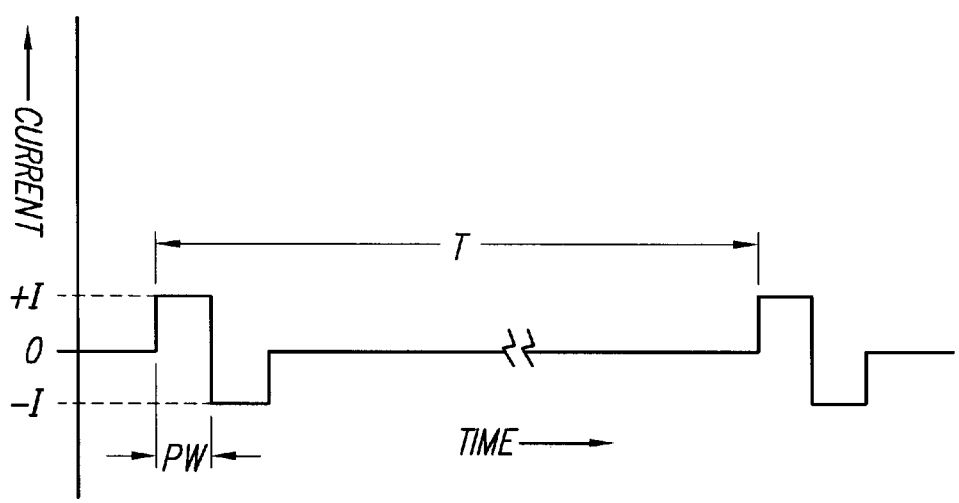
FIG. 2 illustrates a typical current stimulation waveform, and defines stimulus parameter values that are typically used to characterize an electrical stimulus.

FIG. 2 illustrates a typical stimulation pulse waveform that might be used with the IPG 30. The stimulation pulses shown in the waveform of FIG. 2 are biphasic pulses, having a first pulse of one polarity followed immediately by a pulse of the same magnitude but opposite polarity. A biphasic pulse offers the advantage of balancing the electrical charge that flows through the body tissue, which is generally considered to be an important consideration. Other pulse waveforms may also be used to provide a charge balanced condition, as is known in the art.

The waveform shown in FIG. 2 is useful, for purposes of the present invention, because it defines the common stimulus parameters that are used to define the electrical stimuli generated by the IPG 30. These stimulus parameters include, e.g., pulse width (PW), pulse amplitude, and pulse rate. As seen in FIG. 2, the pulse width is the width, measured in units of time (such as microseconds or milliseconds), of the individual pulses that make up the biphasic pulses. The pulse amplitude is the magnitude of the peak current in the pulse, measured in units of electrical current, e.g., milliamperes (mA). In FIG. 2, the amplitude is shown as "I". One pulse of the biphasic pulse has an amplitude of +I, and the other pulse has a magnitude of −I. The stimulation rate is determined by the inverse of the period T between recurring pulses. That is, the rate, expressed in units of pulses per second, or Hz, is equal to 1/T, where T is the time increment between the biphasic (or other) pulses. The pulse rate, depending upon the application, may also be expressed in units of pulses per minute (PPM). The ratio of the pulse width (PW) to the time T (the increment between the pulses) defines the duty cycle.

In accordance with the present invention, once the IPG 30 and the electrode array 40 have been implanted within the patient, the programmer 20, or equivalent device, is used to determine appropriate threshold levels, e.g., the perception threshold levels and the maximum tolerable threshold levels, associated with an electrical stimulus current applied through a selected set or group of electrode contacts 42. Such threshold data typically requires obtaining subjective feedback form the patient as stimuli of various magnitudes are applied through various electrode combinations.

The threshold data, e.g., perception and maximum tolerable threshold data, is stored within the programmer 20, or other device having a memory. FIG. 3A illustrates, by way of example, perception threshold data and maximum tolerable threshold data obtained from four different electrodes sets, identified as electrodes sets "a", "b", "c" and "d". Electrode set "a" might comprise, e.g., electrode contact 42*a* as a cathode combined with reference electrode 32 as an anode (see FIG. 1). Similarly, electrode set "b" might comprise, e.g., electrode contact 42*c* as an anode combined with electrode contact 42*h* as a cathode. Electrode set "c" might comprise, e.g., electrode contacts 42*a*, 42*b* and 42*c*, all as cathodes, combined with electrode contact 42*h*, as an anode. Likewise, electrode set "d" might comprise electrode contacts 42*b* and 42*c*, both as anodes, combined with electrode contacts 42*a* and 42*d*, both as cathodes. It is to be emphasized that such electrode sets are only exemplary of some of the types of electrode sets that could be selected.

As seen in FIG. 3A, the perception thresholds for electrode sets "a", "b", "c", and "d" are measured to be 1 mA, 2 mA, 2 mA and 3 mA, respectively. Similarly, the maximum tolerable thresholds for electrode sets "a", "b", "c", and "d" are measured to be 9 mA, 7 mA, 8 mA and 6 mA, respectively. A key feature of the present invention is that these threshold data, once measured during an initial set up period, are "equalized" so that the equalized threshold levels may thereafter be used as further testing continues to determine other optimum stimulus parameters and electrode configurations, and as subsequent use of the optimum stimulus parameters goes forward.

Equalization is achieved, in accordance with the invention, as shown in FIG. 3B. As seen in FIG. 3B, the perception and maximum tolerable threshold data gathered in FIG. 3A is mapped into unit-less "magnitude level" settings. The magnitude level settings are preferably represented by a number, e.g., the numbers 0 through 10. Alternate representations of the magnitude level may also be employed, e.g., a visual representation, such as bars on a bar chart, or color or gray-scale density of graphical symbols, or the like. In FIG. 3B, magnitude level 1 is defined as the perception threshold of each electrode set. Thus, magnitude level 1 is 1 mA for electrode set "a", 2 mA for electrode set "b", 2 mA for electrode set "c", and 3 mA for electrode set "d". Magnitude level 10 is defined as the maximum tolerable threshold of each electrode set. Thus, magnitude level 10 is 9 mA for electrode set "a", 7 mA for electrode set "b", 8 mA for electrode set "c", and 6 mA for electrode set "d". The magnitude levels between the magnitude levels 1 and 10 are then computed to be an appropriate value that lies between the perception threshold and the maximum tolerable threshold, with the magnitude of the stimulus increasing as the number of the magnitude level increases. For example, the currents associated with magnitude levels 2-9 for electrode set "a" may be determined by assuming a linear increase. That is, assuming a linear relationship, there are eight magnitude level slots that span from 1 mA to 9 mA in equal increments of 8/9 mA, or approximately a 0.89 mA increase for each step up in the magnitude level. Thus, with this assumption, magnitude level 2 for electrode set "a" would be set to 1.89 mA, magnitude level 3 to 1.89 mA+0.89 mA=2.78 ma, and so on, up to magnitude level 10 which is 9 mA.

It should be pointed out that other relationships, i.e., other than linear, may also be assumed for the magnitude level values for each electrode set. Some possible relationships are explained in more detail below, and have particular applicability where more than one electrode serves as an anode and/or cathode.

It should also be pointed out that, while the term "magnitude level" is used herein to describe the unit-less number that is assigned to uniformly denote the stimulus level between the perception and maximum tolerable thresholds for each electrode set, the term "amplitude level" could also be employed inasmuch as it is usually the amplitude which is adjusted in order to change the energy associated with a given stimulus pulse. As is known in the art, however, pulse width also can be used to increase or decrease the energy content of a stimulus pulse. Hence, because either pulse amplitude or pulse width can affect the energy content of the stimulus pulse, the term "magnitude" is used herein as a generic term intended to encompass pulse amplitude and/or pulse width and/or other stimulus parameters that affect the energy content of the delivered electrical stimuli.

Thus, as shown in FIG. 3B, the equalization process involves mapping the raw perception and maximum tolerable threshold data from FIG. 3A (or other threshold data) to the form shown in FIG. 3B, with the perception threshold for each electrode set comprising a first magnitude level, e.g., magnitude level 1, and with the maximum tolerable threshold for each electrode set comprising a second magnitude level, e.g., magnitude level 10. The available magnitude levels between the first and second magnitude levels are then assigned stimulation values that range from the perception threshold value to the maximum tolerable threshold value in accordance with a prescribed relationship, e.g., a linear relationship.

It should also be pointed out that, once some basic measurement data has been taken for a suitable sample size of electrode sets, it may not be necessary to measure the minimum perception threshold level and the maximum tolerable threshold level for each electrode set. Rather, a single threshold point may be measured, e.g., a most comfortable sensation level, which (through empirical or other testing may be determined to be a magnitude level 4 or 5), and thereafter the maximum tolerable threshold level (magnitude level 10) and minimum perception threshold level (magnitude level 1), and all of the intermediate magnitude levels may be estimated.

Additionally, it should be noted that not all electrode configurations need to be measured to determine threshold levels. Rather, a subset of the electrode configurations may be measured, and the magnitude level data for remaining (unmeasured) electrode configurations may thereafter be estimated. For example, assume an in-line electrode array 42 of the type shown in FIG. 1 having eight electrode contacts 42a, 42b, 42c, . . . 42h. Further, assume a monopolar electrode configuration. The only threshold measurements that may be needed are for the end electrodes, i.e., electrode 42a and the reference electrode 32, and the electrode 42h and the reference electrode 32. Once the threshold data for these end electrodes have been measured, then corresponding threshold data may be estimated for the remaining monopolar electrode configurations. For example, suppose the minimum perception threshold for electrode 42h with respect to the reference electrode 32 is 2 mA, while the minimum perception threshold for electrode 42a with respect to the reference electrode 32 is 3.75 ma. The minimum perception thresholds for the remaining monopolar electrode configurations may then be estimated using, e.g., a linear extrapolation approach, wherein the minimum perception threshold for electrode 42b would be 3.5 mA, electrode 42c would be 3.25 mA, electrode 42d would 3 mA, electrode 42e would be 2.75 mA, electrode 42f would be 2.5 mA, and electrode 42g would be 2.25 mA. Estimation methods other than linear extrapolation may also be used. Additionally, once monopolar threshold measurements have been determined, threshold measurements for other configurations, such as bipolar, tripolar, or multipolar, may readily be estimated using appropriate models of the stimulation circuit, as are known in the art.

Figure 4:
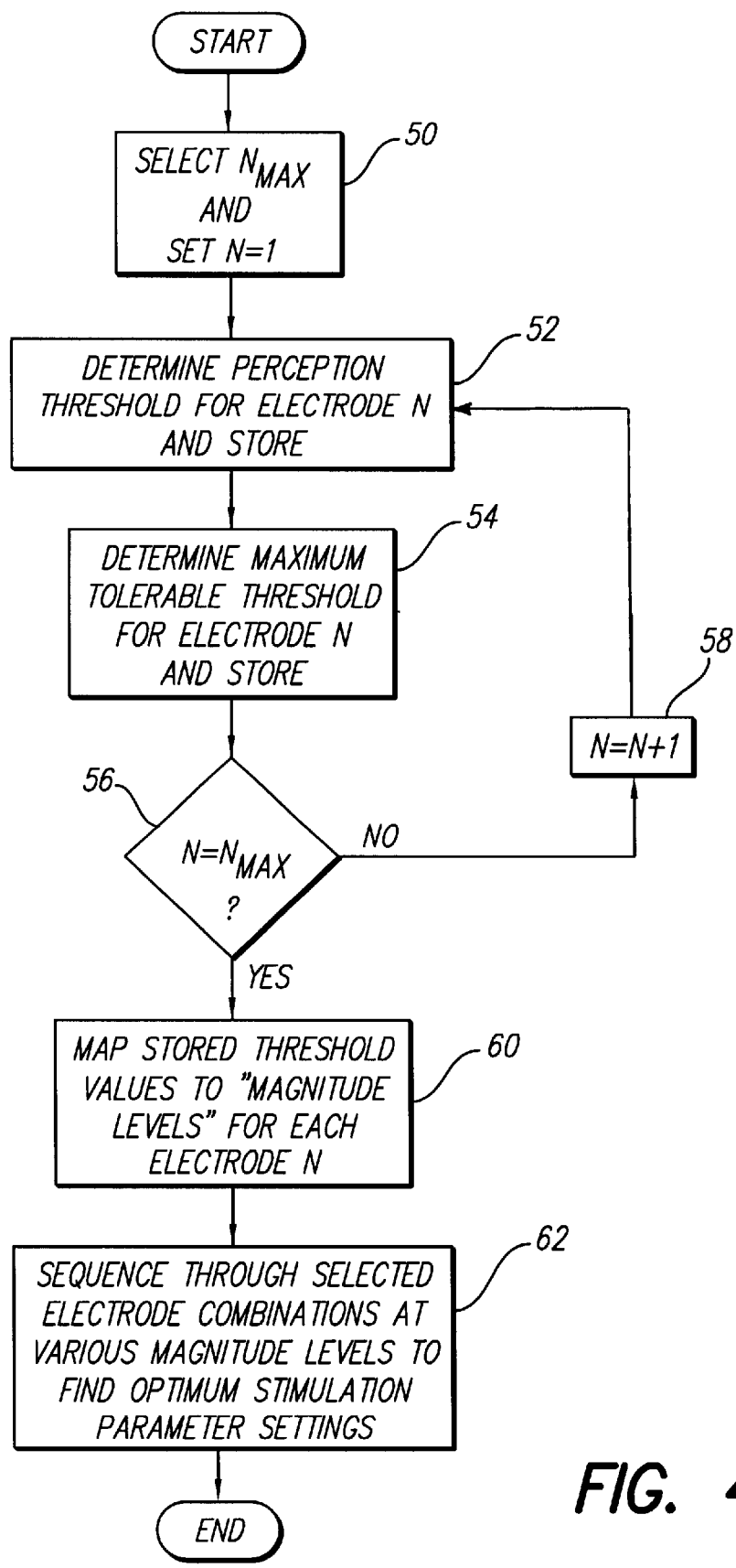
FIG. 4 is a high level flow chart that depicts a method of programming a neural stimulator in accordance with the invention in order to ascertain optimum stimulus parameter values that may be programmed into the neural stimulator.

Turning next to FIG. 4, there is shown a high level flow chart that depicts a method of programming a neural stimulator in accordance with the teachings of the present invention. The goal of such method is to ascertain optimum stimulus parameter values that may be programmed into the neural stimulator. As seen in FIG. 4, a first step (block 50) of the method involves selecting the number of electrode sets, $N_{MAX}$, that are to be used. Some of the electrode sets may include a single electrode paired with the reference electrode (a monopolar configuration), or two electrodes paired together (a bipolar configuration). While a large number of electrode sets could theoretically be used, in practice there will generally be a more manageable number of electrode sets to use based upon the particular application involved and the symptoms experienced by the patient. Also included as an initial step is to set a pointer N to an initial value, e.g., to set N=1. Then, for a first electrode set (N=1), the perception (or other) threshold is determined and stored (block 52). Additionally, if possible, the maximum tolerable threshold is also determined and stored (block 54); although, as indicated above, a single threshold measurement may be all that is required in some instances. This process is repeated for each electrode set (blocks 56, 58) until all of the threshold data has been obtained for each defined electrode set. As indicated above, in some instances, once some initial threshold data has been obtained, the remaining data may be estimated. The gathering of such threshold data thus creates a data set similar to that shown in FIG. 3A.

Next, after the threshold data has been gathered (measured and/or estimated) for each electrode or electrode set, the data is mapped (equalized) to magnitude levels (block 60), with a first level corresponding to the perception threshold, and with a second level corresponding to the maximum tolerable threshold. The mapping of such threshold data thus creates a data set similar to that shown in FIG. 3B. As part of this mapping or equalizing function, the available magnitude level numbers between the perception level and the maximum tolerable threshold are assigned to current stimulus magnitudes that are computed, or otherwise determined, so that the energy content of the applied stimulus increases as the "magnitude level" increases from the perception level to the maximum tolerable level.

Once the magnitude levels for each electrode or electrode set have been determined, the IPG 30 is controlled so as to sequence through selected electrode sets, or combinations of electrodes, at various magnitude levels in order to determine which combinations of electrodes and stimulus parameters produce a desired result (block 62). For a spinal cord stimulator, the desired result will typically be an area or zone of paresthesia that masks or blocks an area or zone of pain. Advantageously, such sequencing may, for the most part, be carried out under automatic control of the IPG 30 and the external programmer 20. Any of numerous different types of sequencing algorithms may be used for this purpose. By adjusting the magnitude of the applied stimulus in terms of the "magnitude level" number, rather than the actual current value, the testing or fitting process (i.e., the process of trying to locate the optimum stimulation parameters and electrode set) may be carried out much quicker and safer than has heretofore been possible. Further, the system may continuously or systematically or under manual control "jump" between two or more electrode sets, thereby allowing the patient to compare which of the two or more electrode sets produces the best (most efficacious) result.

EXAMPLE

In this example, a single in-line electrode array having eight electrode contacts, as shown in FIG. 1, was used. Threshold data measurements, including perception and maximum tolerable, are made for each electrode in both a monopolar and a bipolar configuration. Magnitudes for each electrode are then equalized by assigning magnitude levels of "1" for the perception threshold, and "10" for the maximum tolerable threshold. Each electrode has two stimulation magnitude ranges that are linearly applied depending on the number of cathodes and anode separation. The following relationships and definitions are used in this process:

X=Magnitude Level (0-10), where 0 level=0 mA.
I=mA for electrode (n).
P=Perception Threshold, mA.
M=Maximum Threshold, mA.
E=number of cathodic electrodes in a group.

If X=1, then I=P;
If X=10, then I=M;
If X=0, then I=0;
and for all other values of X, $$I = \frac{(M-P)*(X-1)}{9E} + \frac{P}{E} \quad (1)$$

The field location (stimulus location) is movable. That is, one or more selected cathodes and anodes may be moved as a group by pressing up/down on a suitable programmer control unit, e.g., the programmer 20 (FIG. 1). The orientation of anodes and cathodes with respect to one another remains constant while the group or set of electrodes is moved up or down among the possible programmable electrodes. Magnitude Level X remains constant for all electrodes that become selected by the up/down input, while individual current levels are input for each selected electrode based on the formula presented above in Equation (1).

The size of a "virtual" cathode may be adjusted by increasing or decreasing the number of adjacent electrodes assigned to the "virtual" cathode. Increasing the size of a "virtual" cathode (or "virtual" anode) by increasing the number of adjacent electrodes with an up/down input while maintaining a constant magnitude (amplitude) level causes current summation which may create an increased perception level. That is, while the magnitude (amplitude) level is maintained at a constant for the "virtual" cathode, the current values associated with this constant magnitude level would be distributed among the individual electrodes as they are added or subtracted into the "virtual" cathode. This means that the respective current values (mA) are applied to the distributed level as follows:

$$X = E + \frac{(I_1 - P_1)*9}{E(M_1 - P_1)} + \frac{(I_2 - P_2)*9}{E(M_2 - P_2)} \cdots \frac{(I_n - P_n)*9}{E(M_n - P_n)} \quad (2)$$

As required, one or more constants may be added to Eq. (2) when the effect of summing the amplitudes at the electrodes is not perceived as a constant level.

The current field may also be focused. Focus occurs by selecting anodes to create near and far field current paths. When the anodes are adjacent to the cathodes, the bipolar thresholds are used. In monopolar, the monopolar thresholds are used. As the anodes move away from the cathodes, i.e., as the separation distance between the anodes and cathodes increases, a linear range is extrapolated between the bipolar and monopolar threshold ranges.

Figure 5:
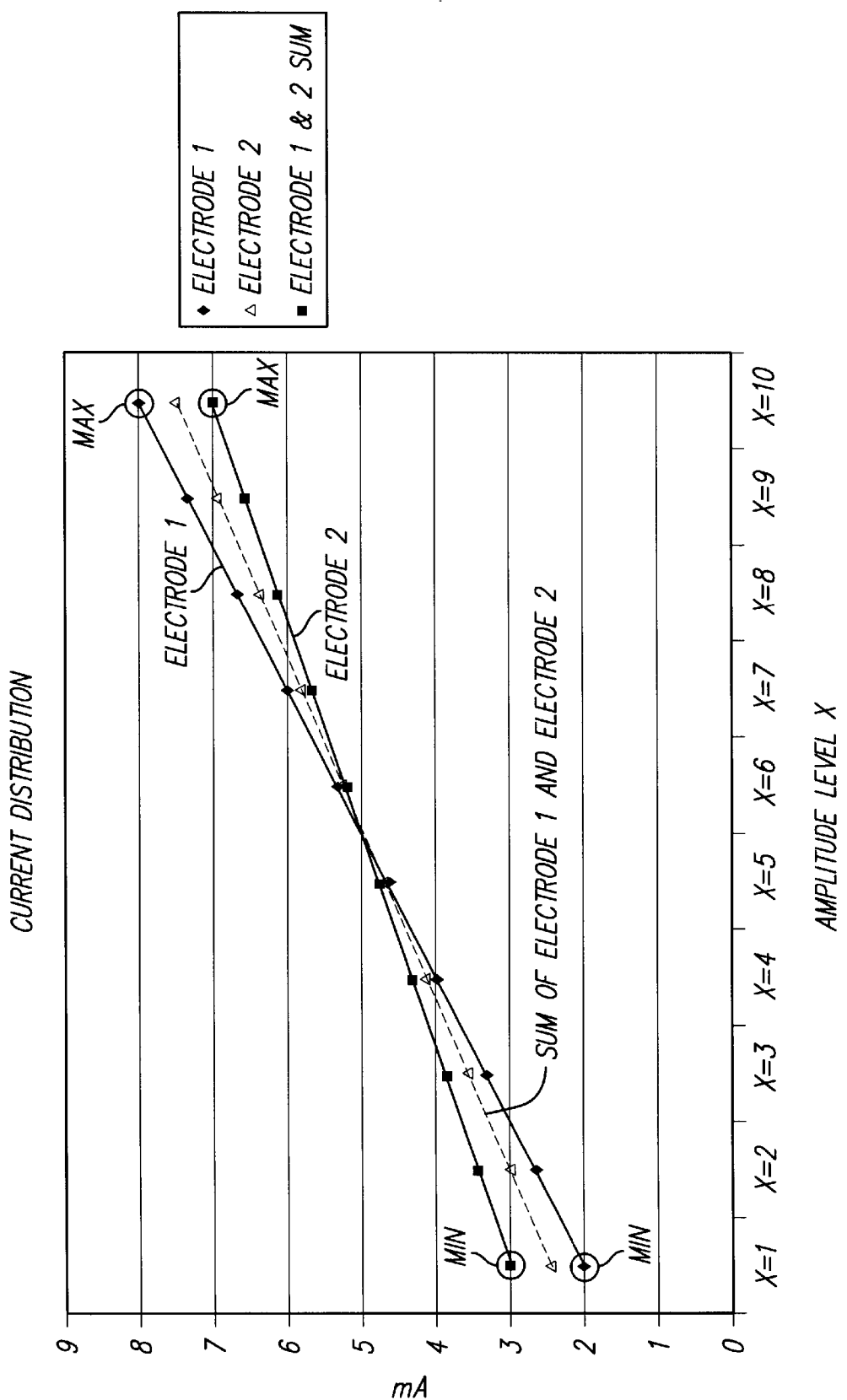
FIG. 5 is a graph illustrating a representative stimulating current distribution for first and second electrodes as a function of amplitude (magnitude) level.

FIG. 5 is a graph that illustrates the current distribution between two electrodes, designated electrode 1 and electrode 2, as well as the current sum realized when the current flow through electrode 1 is summed with the current flow through electrode 2, for magnitude (amplitude) levels ranging between 1-10. FIG. 6 depicts the numerical data associated with the graph of FIG. 5.

Figure 7:
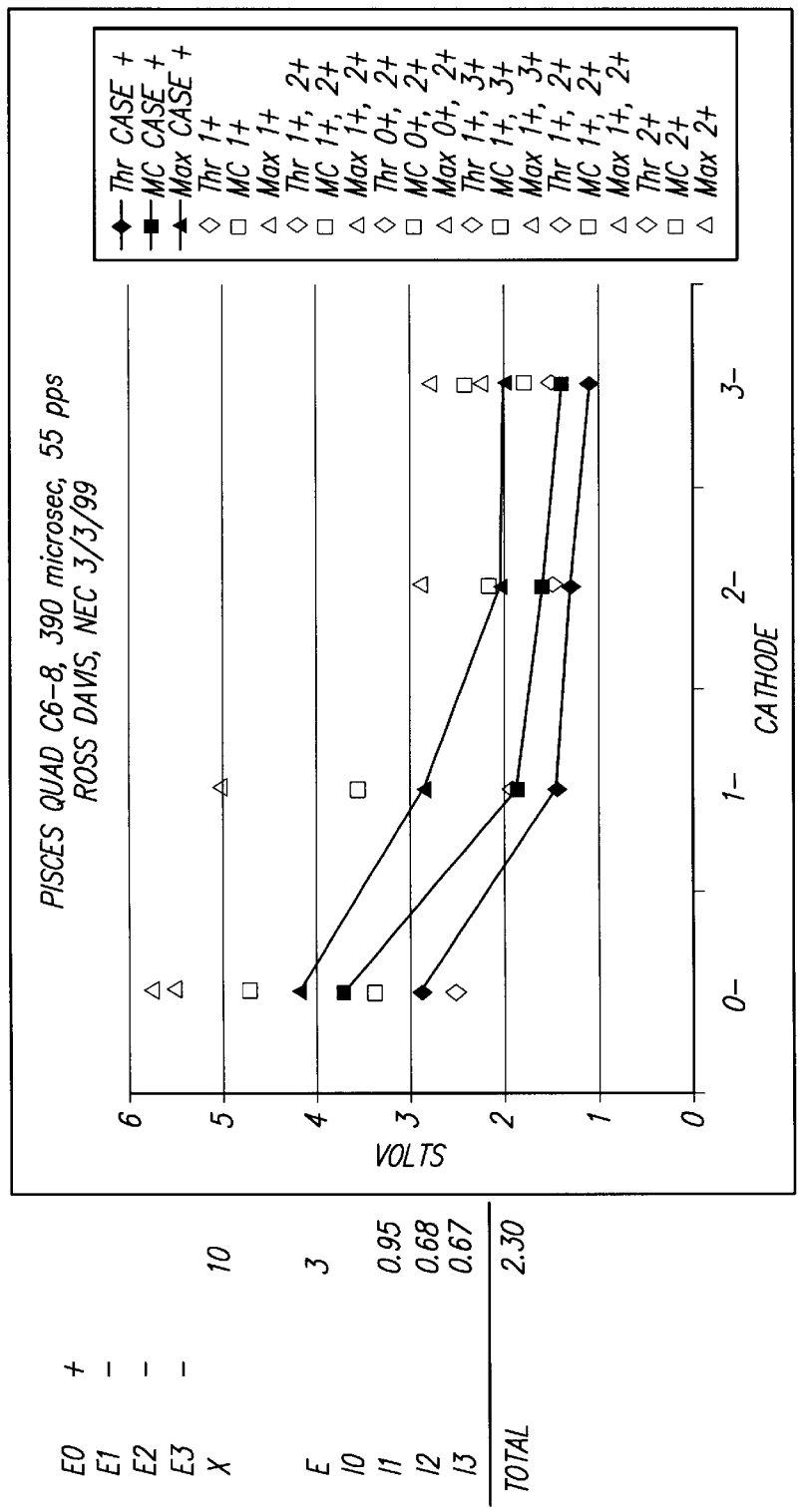
FIG. 7 illustrates patient threshold data in tabular and graphical form for various electrodes associated with a neural stimulator, and further illustrates the concept of current summing when more than two electrodes are included within the stimulation group.

FIG. 7 illustrates patient threshold data in tabular and graphical form for various electrodes associated with the example, and further illustrates the concept of current summing when more than two electrodes are included within the stimulation group.

Figure 8:
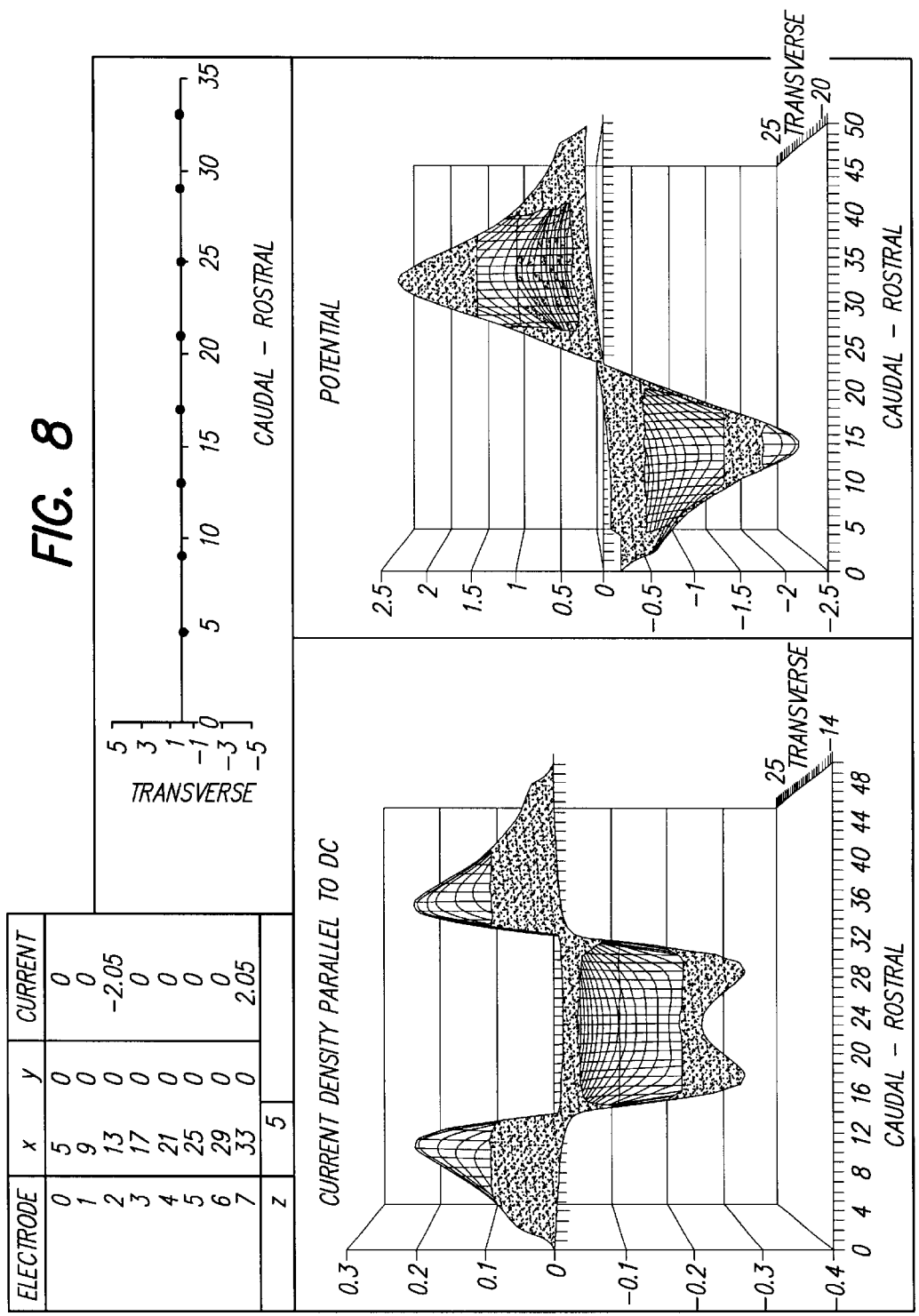
FIG. 8 shows the current and voltage potential distributions obtained at various points along an in-line electrode associated with a stimulus pulse that is applied between electrode two (cathode) and electrode seven (anode) of an in-line electrode having eight electrodes numbered 0 through 7.

By way of example, FIG. 8 shows the current and voltage potential distributions obtained at various points along an in-line electrode associated with a stimulus pulse that is applied between electrode two (cathode) and electrode seven (anode) of an in-line electrode having eight electrodes numbered 0 through 7. Electrode 0 is the most distal electrode, and thus electrode two (cathode) corresponds to electrode contact 42*c* in FIG. 1, and electrode seven (anode) corresponds to electrode contact 42*h* in FIG. 1.

Figure 9:
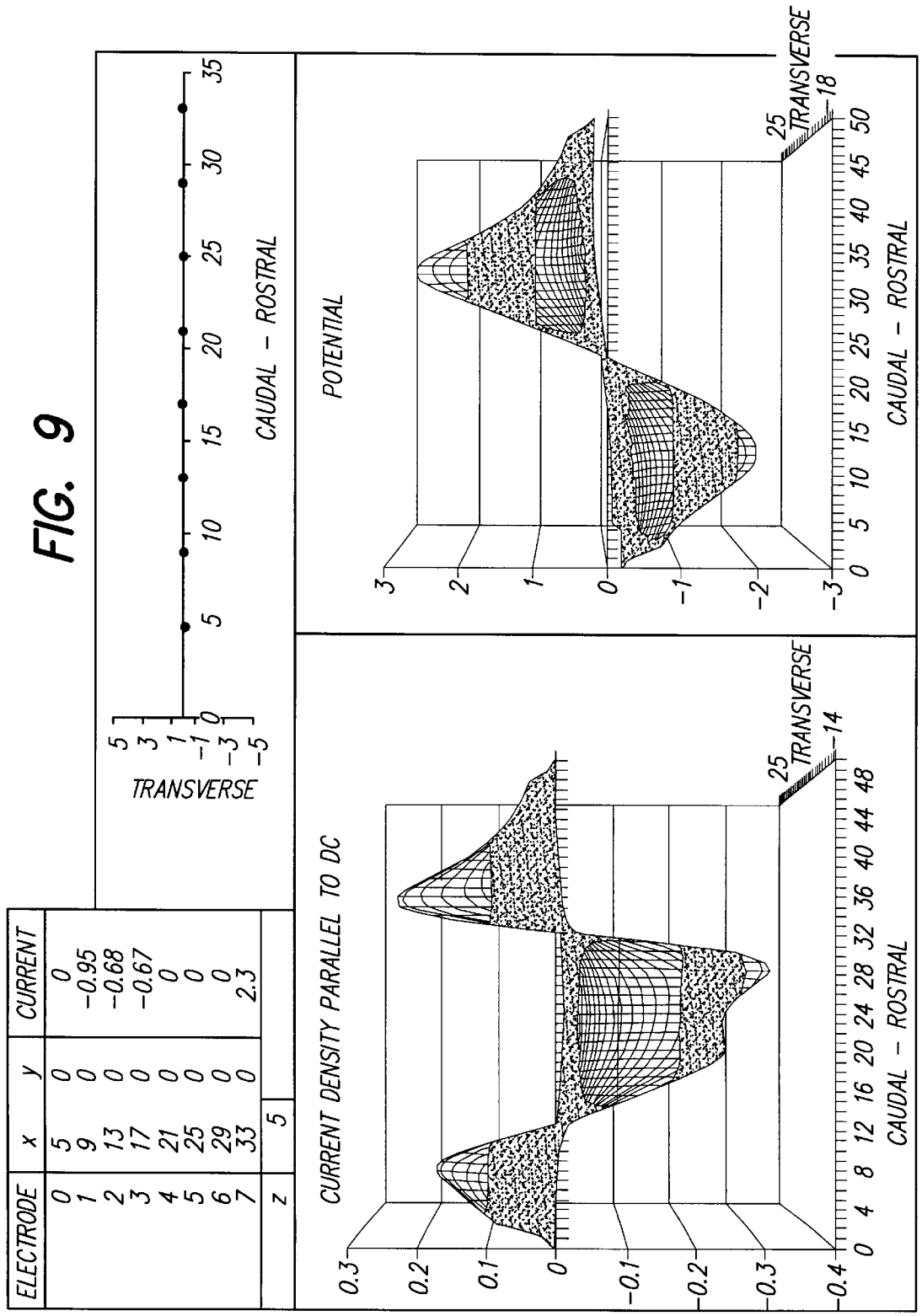
FIG. 9 similarly shows the current and voltage potential distributions obtained at various points along an in-line electrode associated with a stimulus pulse that is applied between electrodes one, two and three (cathodes) and electrode seven (anode) of an in-line electrode having eight electrodes numbered 0 through 7.

Still by way of example, FIG. 9 similarly shows the current and voltage potential distributions obtained at various points along an in-line electrode associated with a stimulus pulse applied between electrodes one, two and three (cathodes) and electrode seven (anode) of an in-line electrode having eight electrodes numbered 0 through 7.

As described above, it is thus seen that the present invention provides a system and method for programming the magnitude of electrical stimuli generated and applied by a neural stimulator. e.g., a spinal cord stimulator. The electrical stimuli are applied through selected groupings of individual electrode contacts of a multi-electrode-contact electrode array attached to pulse generation circuitry as either cathodes or anodes. The electrode array is implanted so that the individual electrode contacts are in contact with the body tissue to be stimulated. Stimulating electrical current pulses, defined by a prescribed set of stimulus parameters, e.g., pulse amplitude, pulse width and pulse repetition rate, are generated and applied to the selected electrode contacts so as to flow from the anode electrodes to the cathode electrodes. As the current pulses flow through the body tissue, the electrical current causes the neural stimulator to carry out its intended function, e.g, triggering a desired neural response or blocking an undesired neural response. A programming system or method is advantageously included as a key part of the invention whereby the perceived magnitude of the applied stimuli is equalized in order to enable quick, automated, and/or interactive selection of the stimulation parameter values that are used by the stimulator.

As further described above, it is seen that the present invention provides the ability to dynamically switch between electrode sets while the stimulation is continuously applied. Such "jumping" or dynamically switching allows immediate comparisons of stimulation to be made without having to reset the stimulation magnitude, and while maintaining a constant perception of intensity or magnitude of stimulation as controlled by unit-less magnitude levels, thereby avoiding over or under stimulation.

As also described above, it is seen that the invention does not require that threshold measurements be taken for all possible electrode configurations. Rather, a subset of the possible electrode configurations may be measured, and from such measurements estimates may be made of the unmeasured thresholds with relative accuracy.

As additionally described above, it is seen that the invention includes the ability to store adjustments made to stimulation levels for estimated electrode thresholds so that the system learns corrections to the estimated equalized levels.

Further, it is seen that the invention allows adjustment and/or compensation of the perception stimulus when the pulse width is changed, or when any other combination of stimulus parameters is changed that affect the energy of the delivered stimulus pulse.

While the invention herein disclosed has been described by means of specific embodiments and applications thereof, numerous modifications and variations could be made thereto by those skilled in the art without departing from the scope of the invention set forth in the claims.

What is claimed is:

1. A method for operating an implantable neural stimulator, wherein the implantable neural stimulator includes a programmable pulse generator circuit housed within a sealed case, an electrode array connected to the neural stimulator, the electrode array having a plurality of electrode contacts, and wherein various combinations of the electrode contacts comprise sets of electrodes through which an electrical stimulus is applied, wherein the method comprises:

(a) measuring and recording at least one perception point for at least a selected subset of the sets of electrodes;

(b) estimating and recording perception points for unmeasured sets of electrodes; and (c) mapping recorded and estimated values to magnitude levels for use with designated stimulation parameters in a set of stimulus parameters that are programmed into said implantable neural stimulator.

2. The method of claim 1 further including storing, calculating, and automatically adjusting magnitude levels when a given set of electrodes is selected as the electrode set through which an electrical stimulus is to be applied.

3. The method of claim 1 wherein mapping recorded and estimated values to magnitude levels comprises mapping the recorded and estimated values to unit-less magnitude numbers.

4. The method of claim 3 further including defining a set of unit-less magnitude numbers corresponding to each set of electrodes, a first magnitude number being mapped to a first stimulus current producing a minimum perception threshold level, and a second magnitude number being mapped to a second stimulus current producing a maximum tolerable threshold level.

5. The method of claim 4 wherein defining the set of unit-less magnitude numbers comprises defining a set of at least three unit-less magnitude numbers for each set of electrodes, the first magnitude number corresponding to the first stimulus current that produces the minimum perception threshold level, the second magnitude number corresponding to the second stimulus current that produces the maximum tolerable threshold level, and a third magnitude number corresponding to a third stimulus current greater than the first stimulus current and less than the second stimulus current that produces a comfortable threshold level.

6. The method of claim 4 wherein defining the set of unit-less magnitude numbers comprises defining a set of ten unit-less magnitude numbers for each set of electrodes, each unit-less magnitude number corresponding to a respective stimulus current, the respective stimulus currents ranging from the first stimulus current associated with the minimum perception threshold level and the second stimulus current associated with the maximum tolerable threshold level.

7. The method of claim 3 further including
applying a stimulus through a first set of electrodes having a magnitude defined by a selected magnitude number,
applying a stimulus through a second set of electrodes having a magnitude defined by the same selected magnitude number,
comparing the result of the stimulus applied through the first set of electrodes with the result of the stimulus applied through the second set of electrodes in a comparison test, and
selecting stimulus parameters for programming into the implantable neural stimulator as a function of the comparison test.

8. The method of claim 1 wherein estimating and recording perception points for unmeasured sets of electrodes comprises:

determining electrode sets for which perception points have not been measured;

estimating perception points for the unmeasured sets of electrodes by determining the perception points for the unmeasured sets of electrodes as a function of the perception points of the measured sets of electrodes; and recording the estimated perception points.

9. The method of claim 8 further including calculating the perception points comprises extrapolating the perception points for the unmeasured sets of electrodes from the perception points from the measured sets of electrodes.

10. An implantable neural stimulator comprising:

(a) pulse generation circuitry housed within a sealed case, said pulse generation circuitry being adapted to generate electrical stimuli in accordance with programmed stimulus parameters;

(b) an implantable electrode array having a multiplicity of electrode contacts, wherein each of the multiplicity of electrode contacts is selectively connected to the pulse generation circuitry, and wherein the electrode contacts are grouped in selected electrode sets through which the electrical stimuli generated by the pulse generation circuitry is directed, each electrode set including a plurality of the electrode contacts, wherein one of the electrode contacts comprises the sealed case wherein the pulse generation circuitry is housed;

(c) a known threshold level for at least a plurality of the multiplicity of electrode contacts, where said known threshold levels are expressed in units of current or voltage; and (d) an equalizer circuit that equalizes the threshold levels to unit-less magnitude levels.

11. The neural stimulation system of claim 10 wherein the equalizer circuit further estimates threshold levels for electrode contacts not initially known.

12. The neural stimulation system of claim 11 further wherein the neural stimulator automatically adjusts the magnitude of the stimulus applied through a selected electrode set to a value determined from the unit-less magnitude levels for the selected electrode set.

13. A system for determining an optimal set of stimulus parameters to be programmed into implantable pulse generation circuitry, the implantable pulse generation circuitry being housed within a sealed case, the pulse generation circuitry being adapted to generate electrical stimuli in accordance with programmed stimulus parameters; and further wherein an electrode array having a plurality of electrode contacts is selectively connected to the pulse generation circuitry; said system comprising:

at least one measured perception threshold for a selected set of the plurality of electrode contacts, where said at least one perception threshold is measured in units of current or voltage;

an equalizer that equalizes the at least one measured perception threshold for the selected set of electrode contacts to a unit-less magnitude level, and that estimates perception thresholds and corresponding magnitude levels for sets of electrode contacts where perception thresholds have not been measured; and means for automatically adjusting the magnitude of the electrical stimuli applied by an implantable neural stimulator through a selected set of electrode contacts as a function of unit-less magnitude levels associated with the selected set of electrodes.

14. The system of claim 13 wherein the equalizer comprises:

memory circuitry wherein the perception threshold is stored;

mapping means for mapping the perception threshold of a given set of electrode contacts to a first number magnitude level, wherein when a stimulus having the first number magnitude level is selected to be applied to a selected set of electrode contacts, the set of electrode contacts receives a stimulus having a magnitude equal to the perception threshold.

15. The system of claim 14 wherein there are at least two perception thresholds for each selected set of the plurality of electrode contacts, one perception threshold comprising a minimum perception threshold level, and another perception threshold comprising a maximum tolerable threshold level; and wherein the mapping means maps the minimum perception threshold level to the first number magnitude level, and maps the maximum tolerable threshold level to a second number magnitude level; wherein the selected set of electrode contacts receives a stimulus having a magnitude equal to or near the minimum perception threshold level when the first number magnitude level is selected, and wherein the selected set of electrode contacts receives a stimulus having a magnitude equal to or near the maximum tolerable perception threshold level when the second number magnitude level is selected.

16. The system of claim 15 wherein the first number magnitude level comprises a low number, and the second number magnitude level comprises a high number, and further wherein a plurality of number magnitude levels exist greater than the low number and less than the high number, and wherein the pulse generation circuitry generates a stimulus having a magnitude greater than the minimum perception threshold level and less than the maximum tolerable threshold level when one of the number magnitude levels between the low and high numbers is selected as the magnitude level of the stimulus to be applied through a given set of electrode contacts.

17. The system of claim 16 wherein the low number comprises the number "1", and the high number comprises the number "10", and further wherein any of the number magnitude levels "1" through "10" is selected as the magnitude level of the stimulus that is to be applied through the selected set of electrode contacts.

18. The system of claim 17 wherein the number "0" is selected as a magnitude level, and wherein the magnitude of a stimulus having a magnitude level "0" is zero or off.

19. The system of claim 13 wherein at least one of the plurality of electrode contacts comprises a reference electrode contact located integrally with the sealed case of the implantable neural stimulator.

20. A neural stimulation system comprising:

implantable pulse generation circuitry housed within a sealed case, said pulse generation circuitry being adapted to generate a stimulus pulse in accordance with programmed stimulus parameters;

an electrode array having a multiplicity of electrode contacts, wherein each of the multiplicity of electrode contacts is selectively connected to the pulse generation circuitry;

wherein a minimum perception threshold and a maximum tolerable threshold for each of the multiplicity of electrode contacts is known or determinable, wherein said thresholds are measured in units of current or voltage; and an equalizer that equalizes the minimum perception threshold and the maximum tolerable threshold to unit-less magnitude levels; and wherein the pulse generation circuitry, upon command, automatically adjusts the magnitude of the stimulus pulse applied through a selected combination of the multiplicity of electrode contacts to a level referenced to the unit-less magnitude levels.

21. The neural stimulation system of claim 20 wherein the equalizer comprises:

memory circuitry wherein the minimum perception threshold and the maximum tolerable threshold are stored;

a mapping circuit that maps the minimum perception threshold of each electrode contact to a first number magnitude level and that maps the maximum tolerable threshold to a second number magnitude level, wherein when a stimulus having the first number magnitude level is selected to be applied to a selected combination of electrode contacts, the selected combination of electrode contacts receives a stimulus having a magnitude equal to or near the minimum perception threshold, and when a stimulus having the second number magnitude level is selected to be applied to a selected combination of electrode contacts, the selected combination of electrode contacts receives a stimulus having a magnitude equal to or near the maximum tolerable threshold.

22. The neural stimulation system of claim 21 wherein the first number magnitude level comprises a low number, and the second number magnitude level comprises a high number, and further wherein a plurality of levels exist greater than the low number and less than the high number, and wherein the implantable neural stimulator generates a stimulus having a magnitude greater than the minimum perception threshold and less than the maximum tolerable threshold when one of the levels between the low and high numbers is selected as the magnitude level of the stimulus to be applied to a selected combination of electrode contacts.

23. The neural stimulation system of claim 22 wherein the low number comprises the level "1", and the high number comprises the level "10", and further wherein any of the levels "1" through "10" is selected as the magnitude level of the stimulus applied through a selected combination of electrode contacts; and wherein the implantable neural stimulator generates a stimulus having a magnitude greater than the minimum perception threshold measurement and less than the maximum tolerable threshold measurement when one of the levels "2" through "9" is selected as the magnitude level of the stimulus to be applied to the selected combination of electrode contacts.

* * * * *

UNITED STATES PATENT AND TRADEMARK OFFICE
CERTIFICATE OF CORRECTION

PATENT NO.     : 6,587,724 B2
DATED          : July 1, 2003
INVENTOR(S)    : Carla M. Mann It is certified that error appears in the above-identified patent and that said Letters Patent is hereby corrected as shown below:

<u>Title page,</u>
Item [75], Inventor, change to -- Carla Mann Woods --.

Signed and Sealed this

Twenty-third Day of December, 2003

JAMES E. ROGAN
*Director of the United States Patent and Trademark Office*